(12) United States Patent
Sivasankar et al.

(10) Patent No.: US 8,088,977 B2
(45) Date of Patent: Jan. 3, 2012

(54) REGULATORY ELEMENTS ASSOCIATED WITH CBF TRANSCRIPTION FACTORS OF MAIZE

(75) Inventors: Shoba Sivasankar, Urbandale, IA (US); Timothy G. Helentjaris, Tucson, AZ (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 153 days.

(21) Appl. No.: 12/207,620

(22) Filed: Sep. 10, 2008

(65) Prior Publication Data

US 2009/0138986 A1    May 28, 2009

Related U.S. Application Data

(60) Provisional application No. 60/971,278, filed on Sep. 11, 2007.

(51) Int. Cl.
*A01H 1/00* (2006.01)
*C07H 21/04* (2006.01)
*C12N 15/00* (2006.01)
*C07K 14/415* (2006.01)

(52) U.S. Cl. ......... 800/287; 435/6.1; 435/468; 435/419; 435/320.1; 530/350; 530/370; 536/24.1; 800/278; 800/295; 800/320

(58) Field of Classification Search ............. 435/6, 69.1, 435/468, 419, 320.1, 6.1; 536/24.1; 800/278, 800/295; 530/370

See application file for complete search history.

(56) References Cited

U.S. PATENT DOCUMENTS

| 2005/0235382 A1 | 10/2005 | Ahrens et al. |
| 2006/0162027 A1 | 7/2006 | Sivasankar et al. |
| 2007/0209085 A1 | 9/2007 | Wu et al. |

OTHER PUBLICATIONS

Shinwari, Z., et al.; "An *Arabidoposis* Gene Family Encoding DRE/CRT Binding Proteins Involved in Low-Temperature-Responsive Gene Expression"; Biochemical and Biophysical Research Communications (1998) 250:161-170; Elseiver, Oxford, UK.

Kusano, T., et al.; "A maize DNA-binding factor with a bZip motif is induced by low temperature"; Mol Gen Genet (1995) 248:507-517; Springer-Verlag; The Netherlands.

Wilson, R.K., et al.; "The Sequence of *Zea mays* bac clone CH201-328C21"; EMBL Genebank Accession No. AC203745; May 17, 2007.

Zarka, D.G., et al.; "Cold Induction of *Arabidopsis* CBF Genes Involves Multiple Ice (Inducer of CBF Expression) Promoter Elements and a Cold-Regulatory Circuit That Is Desensitized by Low Temperature"; Plant Physiology (Oct. 2003) 133:910-918; American Society of Plant Biologists; Rockville, MD, US.

Wilson, R.K., et al.; "The Sequence of *Zea mays* bac clone CH201-261E8"; EMBL Genebank Accession No. AC199509; Mar. 13, 2007.

*Primary Examiner* — Phuong Bui

(57) ABSTRACT

Compositions and methods for regulating expression of heterologous polynucleotide sequences in a plant are provided. Compositions are novel nucleotide sequences comprising an isolated stress-induced promoter natively linked to the maize CBF1 or CBF2 coding region. A method for expressing a heterologous polynucleotide sequence in a plant using the regulatory sequences disclosed herein is provided. The method comprises transforming a plant cell to comprise a heterologous polynucleotide sequence operably linked to one or more of the regulatory sequences of the present invention and regenerating a stably transformed plant from the transformed plant cell.

19 Claims, 3 Drawing Sheets

Figure 1. Regulatory sequence of ZmCBF1

```
-1329 CCATATCGAA TCCGAATCCA AAGTTGTACT ATTTTACTAC TATCTATCTA

-1279 TTAACCTATA TCCATCACGA ATATAAAAGT ATCTAAGTTA TTAGTGAAAA

-1229 AATGTATTTA TTTATAGTAT CTATATCCGG TACCCTCGCC CCTATCTATA

-1179 TCTCATCCAC GACACGAGCG GTGGACCACA CACGACACTG GGGAAACTGG

-1129 AAAATTTCCG CATTTTCATC CCGGCTTCTG CTGGAACTGA AGTACTAGT

-1079 AAGTAAGCTA CGGCGGTTCG TCCTGGATGT GGATGGGCGG CCCACGCGTG

-1029 CAGTGCTTGT GCTTCTTGAT CACTGACGAC CCGGTCGCCT GGCCCAACCC

-979 GGGCAGGCCA CGTCGAACCC CGTCTCCATC CCCTCGGCGG GTGATGGATT

-929 CGGTGGGGCC GGGGCGGGAG GAGATCGAGT AGCAGACGGC GACACCCGAT

-879 CATCAAGCGT TGAGCGCGGA GGACGCAAGG GCGGACGCGC GGCTACATCG

-829 AAACGAGTCC GGACGAGGAG GAGCGGAGGC AGGCGCCTCC GGTCGGTGTC

-779 GGGGGCGGCG GCAGGCAGGT AGCCCCACGC GTTTCCGCGG GCGGCGCCAC

-729 GGCCCTGTCT CCGAGCTGGA AATGATCAAC AAGCCGACGG AAAACCAGTG

-679 GCCTGCCGCC GCCGCCGCAC CGCATGGCGC ATGTGCCGAA GCCCACCGGC

-629 CGCCGTCACG TGCCCTGCCC ACGGCTCTGA TATTTTTTTT ATTATTGATT

-579 CTATTCTACG TTGCCCTGCT AGATTTTTTT CTTCTTCCTT TTTAGAGATT

-529 CTCTGTGTGC CCTGCTGATT CTCGGTGTTG TCAGTGAAGC GAGCGAAAGA

-479 CCGAAGAGGT CTGCCGCCGC CCAAAAGCCA GCCGTTGTCG CCATCTCCAC

-429 GTGGCCATCT CCTGATCCTC TGTCGCTGCC ATGGCGGGGG CCCTGCCGCA

-379 TGTCAGTCCG CGCGACTTTC CTTAACGGCG ACTGCTAAGC AATGGGAATG

-329 GGATGGGAGT GGAGCCGACG ACGCCACGCT GACGCCAACG CGTCTTCCCC

-279 CGCCGCCTCG CCACCGTCCC GCACGCAGCA CTGTCCCCGA CTCCCCCAGC

-229 CAGTCTCCAG CTCACACCTC CCAAGTCCCG CCACGCGCCC GCCCAACTGA

-179 CTGACTCCCG CCTTCAAACT TCTCCCGCTC CTCCTGATCC ACGTACCACC

-129 AAATCCTATA TATATAAACC AGACCACAAC TCCCGACTCC ATCCATCGCC

-79 AGCCACGCCA TCAGCCATCG CGTTCCGCAT CGAACCAGCA CATCGCAAGA
                                            ↓
  -29 CAAGCAGCAG CAGCCACCAC TGCCATCACA TGGAGTACGC CGCCGTCGGC

+11 TACGGCTACG GGTACGGGTA CGA
```

Figure 2. Regulatory sequence of ZmCBF2

```
-2209  AACTTCTTGT CTGGTCATTT AGGATTCTGA ACACTCATAC GTCAGCTCAC

-2159  ATCGGTTTGG ACG[CCGAC]TG TACGGATGTG AGCAGACGCT GGTCGATCTC

-2109  CTTTTCCTAT ACTAGCTCTT ATATAAATAC CACCTTTTCG CATTGATTGG

-2059  TGGCCGCCGC TGAGTTCTCT ACTCGGGTGA ACGGAGGGGA GGAGCAGGAG

-2009  ACAGGGGGGA AGCACCTCCC ACGACTTTGG CAGGCCGAAC CGAACGCCAC

-1959  AAAAGTAGGA TTTTTCTCCG GTTCCCCGGG AACAGTCTTT TTCTTCTACT

-1909  GGCAGAAACG GACGGTT[CAG GTG]CGGGAGC TTCCCGGCTG CTGCTGCTGC

-1859  CGCCGGCCTT TTTGCGATAC CATACTGGGG GTTTGGCCCC GGGAATGCTG

-1809  GATTGGGTTT TGTTCGTGGT ACTCTTGGTT TCGGGACTCA T[CACCTG]GTA

-1759  ATGTCGCTAT CGGGTGGATG GATCTCGGCG ACGCGAGACG TACACTGATT

-1709  TCTTTTTCTT TTTTCTTTAT CAATCAGTTA TCAGTACGTA CTGCTACCTA

-1659  GGGTCCTCTC TTTTTTTTCC CCGGATGCAA AATACGTACT GCCTGTAACC

-1609  AATATTATAT TTATATAGAT AAAAACAACA TAAATTTTAA GTCCCTATGT

-1559  TTATCTGAAA ATTTAGAACA GCAATAGTCA TTTCAGTGGA CCAAAGGATT

-1509  GGGTTAGAAT CTGGACAGTG ATTGCGGGAG AAGTCCTGCC ATGAGCTTAG

-1459  GGTCCTAGTT TGGCAACTCC ATCTTTCTAA GGCCTTGTTC GTTTGTGTCG

-1409  GATTACACCC GAAATCGTTA CAGCTAATCA AGTTTATAT AAATTAGAGA

-1359  AGCAATCCGG ATAGGAATCG TT[CCGAC]CCA CCAATCCGCC ACAAACGAAC

-1309  AAGGCCTAAA GATTTCATC TTTCCAAAGA AAATAAACT AAACTTTCTT

-1259  GGAAAAAAAT ATAAATCTCT TAAAAAATGT GGTTGCCAAA CTAGCCCTTA

-1209  TAATAAAGGA AAAACTGGAG GAATTTTAGA GGAATGAAAT CCTATATGAA

-1159  ATTATGTTAT GTGGCCTTTG AAACAGAGGC TTTAGTTCCT ACATATCCTA

-1109  TAAGGTTCCT ATGGAATGGT CCATCGTAGT GATATTTTAG AGAATTTCTA

-1059  ACTTAAAGC[C CGAC]CTCTTA GAAATTGT[CA TTTG]TGCCTC TCTCTCTGCA

-1009  CTCTAATT[CA TGTG]TTCTTT CTATGTTGCA TCCAGGATTC TCAAAACACG

-959   GAAATAGGAG AAA[CACATG]A TTATAACGCC CATGCCGTTG AAATCCTACA

-909   AAAATTTATA ACACGGAAAA GTTATAAAAA CATGTTTTTG GATCATGCGC
```

Figure 2 (continued). Regulatory sequence of ZmCBF2

```
-859  ATAAAAAATA TAGGAATGTG AGACACAAAG AAAATAAAAT ATGAGGGTGG
-809  ACCTCACGCT TAATTTTCCC TCCAAAATTA CCATGGAGCA TGTCATTTCA
-759  TAGGATTTTT CAAGGAATTG ATAGGATCCA ATCATTTGTC CCAAAAGGCT
-709  TTTATATGAA AACTTTCTAT GCGAATTGAA TCCTCTAAAG TTCCTTTGTT
-659  TTTCCTCCAT TCCAAAGTTA TCTGCGTTTT TAATTCATGT ATGATTACAA
-609  GTGTTATACA ACTCTATTCG TACATTTTTT TTCCTTTCTA TTTTTGTATT
-559  TTGTCAATCC TCTGTTCCAA AGGAGGCATC TAAAATAGGG AATGAGATAG
-509  CCTTAATCGA GTACTAGTAG CATTTGATAT ATCATAAAAA AGTAGCATTT
-459  GATATGTGCG AGAAGAGCTG GGGTTAACGT CGTAACGCAA ATAGTTAACT
-409  AGACGGAAAC CGGTAGCGGA AACAAAATCA GCCTTGTGGC CGCAACTACA
-359  CCAAATAGCA CCATCAAGTC ACTATCGAAA TCGCCCTGTT GCCTCCCTAC
-309  TTGCAAGCTG GAAGCTGCAA CTTGCGTCCC CGTCCAGCCG TCCTTGCTCT
-259  CTGACCCAGA TGCAGCCCCC TTCCTTCCCC AGTGCCTGGT GGCTCCCCTC
-209  CCGCGTTATT CACTCTGCTA GTCCTGCTCA GGTCTGCTGA CTGCTGCTCT
-159  CTGATCCAAA CCTCCTCCTC CACCACCACC TATAAATACG CATCCTCAAA
-109  TCCACCATTC CCAAATCGAA AACCACTCGA ACACAAGCTC AGGCAAGCA
 -59  AAAGGAACCC GCACCATCCG AGGCTCAAGC AGAGAAGTGA TCATCATCAT
                                   ↓
  -9  CAGAAGAAGA TGTGCCCAAC CAAGAAGGGG ATGACCGGAG AGCCGAGCTC
 +42  GCCATGCAGC TCGGCA
```

SEQUENCE LISTING

```
<160> NUMBER OF SEQ ID NOS: 2

<210> SEQ ID NO 1
<211> LENGTH: 1373
<212> TYPE: DNA
<213> ORGANISM: Zea mays
<220> FEATURE:
<221> NAME/KEY: misc_binding
<222> LOCATION: (634)...(638)
<223> OTHER INFORMATION: CRT/DRE consensus
<220> FEATURE:
<221> NAME/KEY: misc_binding
<222> LOCATION: (680)...(685)
<223> OTHER INFORMATION: putative myc-binding site
<220> FEATURE:
<221> NAME/KEY: misc_binding
<222> LOCATION: (707)...(712)
<223> OTHER INFORMATION: ABRE core motif
<220> FEATURE:
<221> NAME/KEY: misc_binding
<222> LOCATION: (898)...(903)
<223> OTHER INFORMATION: ABRE core motif
<220> FEATURE:
<221> NAME/KEY: misc_binding
<222> LOCATION: (1015)...(1019)
<223> OTHER INFORMATION: CRT/DRE consensus
<220> FEATURE:
<221> NAME/KEY: misc_binding
<222> LOCATION: (1087)...(1091)
<223> OTHER INFORMATION: CRT/DRE consensus
<220> FEATURE:
<221> NAME/KEY: misc_binding
<222> LOCATION: (1144)...(1149)
<223> OTHER INFORMATION: putative myc-binding site
<220> FEATURE:
<221> NAME/KEY: TATA_signal
<222> LOCATION: (1213)...(1218)
<220> FEATURE:
<221> NAME/KEY: misc_binding
<222> LOCATION: (1233)...(1237)
<223> OTHER INFORMATION: CRT/DRE consensus
<220> FEATURE:
<221> NAME/KEY: misc_binding
<222> LOCATION: (1327)...(1332)
<223> OTHER INFORMATION: putative myc-binding site
<220> FEATURE:
<221> NAME/KEY: misc_feature
<222> LOCATION: (1330)...(1332)
<223> OTHER INFORMATION: translation start site

<400> SEQUENCE: 1
ccatatcgaa tccgaatcca aagttgtact attttactac tatctatcta ttaacctata      60
tccatcacga atataaaagt atctaagtta ttagtgaaaa aatgtattta tttatagtat     120
ctatatccgg taccctcgcc cctatctata tctcatccac gacacgagcg gtggaccaca     180
cacgacactg gggaaactgg aaaatttccg cattttcatc ccggcttctg ctggaactga     240
```

-continued

```
aagtactagt aagtaagcta cggcggttcg tcctggatgt ggatgggcgg cccacgcgtg    300
cagtgcttgt gcttcttgat cactgacgac ccggtcgcct ggcccaaccc gggcaggcca    360
cgtcgaaccc cgtctccatc ccctcggcgg gtgatggatt cggtggggcc ggggcgggag    420
gagatcgagt agcagacggc gacacccgat catcaagcgt tgagcgcgga ggacgcaagg    480
gcggacgcgc ggctacatcg aaacgagtcc ggacgaggag gagcggaggc aggcgcctcc    540
ggtcggtgtc gggggcggcg gcaggcaggt agccccacgc gtttccgcgg gcggcgccac    600
ggccctgtct ccgagctgga aatgatcaac aagccgacgg aaaaccagtg gcctgccgcc    660
gccgccgcac cgcatggcgc atgtgccgaa gcccaccggc cgccgtcacg tgccctgccc    720
acggctctga tattttttt  attattgatt ctattctacg ttgccctgct agattttttt    780
cttcttcctt tttagagatt ctctgtgtgc cctgctgatt ctcggtgttg tcagtgaagc    840
gagcgaaaga ccgaagaggt ctgccgccgc ccaaaagcca gccgttgtcg ccatctccac    900
gtggccatct cctgatcctc tgtcgctgcc atggcggggg ccctgccgca tgtcagtccg    960
cgcgactttc cttaacggcg actgctaagc aatgggaatg ggatgggagt ggagccgacg   1020
acgccacgct gacgccaacg cgtcttcccc cgccgcctcg ccaccgtccc gcacgcagca   1080
ctgtccccga ctcccccagc cagtctccag ctcacacctc ccaagtcccg ccacgcgccc   1140
gcccaactga ctgactcccg ccttcaaact tctcccgctc ctcctgatcc acgtaccacc   1200
aaatcctata tatataaacc agaccacaac tcccgactcc atccatcgcc agccacgcca   1260
tcagccatcg cgttccgcat cgaaccagca catcgcaaga caagcagcag cagccaccac   1320
tgccatcaca tggagtacgc cgccgtcggc tacggctacg ggtacgggta cga           1373
```

<210> SEQ ID NO 2
<211> LENGTH: 2266
<212> TYPE: DNA
<213> ORGANISM: Zea mays
<220> FEATURE:
<221> NAME/KEY: misc_binding
<222> LOCATION: (64)...(68)
<223> OTHER INFORMATION: CRT/DRE consensus
<220> FEATURE:
<221> NAME/KEY: misc_binding
<222> LOCATION: (318)...(323)
<223> OTHER INFORMATION: putative myc-binding site
<220> FEATURE:
<221> NAME/KEY: misc_binding
<222> LOCATION: (442)...(447)
<223> OTHER INFORMATION: putative myc-binding site
<220> FEATURE:
<221> NAME/KEY: misc_binding
<222> LOCATION: (873)...(877)
<223> OTHER INFORMATION: CRT/DRE consensus
<220> FEATURE:
<221> NAME/KEY: misc_binding
<222> LOCATION: (1160)...(1164)
<223> OTHER INFORMATION: CRT/DRE consensus
<220> FEATURE:
<221> NAME/KEY: misc_binding
<222> LOCATION: (1179)...(1184)
<223> OTHER INFORMATION: putative myc-binding site
<220> FEATURE:
<221> NAME/KEY: misc_binding
<222> LOCATION: (1209)...(1214)
<223> OTHER INFORMATION: putative myc-binding site
<220> FEATURE:
<221> NAME/KEY: misc_binding
<222> LOCATION: (1264)...(1269)
<223> OTHER INFORMATION: putative myc-binding site
<220> FEATURE:
<221> NAME/KEY: misc_binding
<222> LOCATION: (1483)...(1488)
<223> OTHER INFORMATION: putative myc-binding site

```
<220> FEATURE:
<221> NAME/KEY: misc_binding
<222> LOCATION: (1598)...(1603)
<223> OTHER INFORMATION: putative myc-binding site
<220> FEATURE:
<221> NAME/KEY: misc_binding
<222> LOCATION: (1721)...(1726)
<223> OTHER INFORMATION: putative myc-binding site
<220> FEATURE:
<221> NAME/KEY: misc_binding
<222> LOCATION: (1746)...(1751)
<223> OTHER INFORMATION: putative myc-binding site
<220> FEATURE:
<221> NAME/KEY: misc_binding
<222> LOCATION: (1957)...(1962)
<223> OTHER INFORMATION: putative myc-binding site
<220> FEATURE:
<221> NAME/KEY: TATA_signal
<222> LOCATION: (2081)...(2086)
<220> FEATURE:
<221> NAME/KEY: misc_feature
<222> LOCATION: (2190)...(2196)
<223> OTHER INFORMATION: putative transcription start site
<220> FEATURE:
<221> NAME/KEY: misc_feature
<222> LOCATION: (2210)...(2212)
<223> OTHER INFORMATION: translation start site

<400> SEQUENCE: 2
aacttcttgt ctggtcattt aggattctga acactcatac gtcagctcac atcggtttgg      60
acgccgactg tacggatgtg agcagacgct ggtcgatctc cttttcctat actagctctt     120
atataaatac cacctttcg cattgattgg tggccgccgc tgagttctct actcgggtga     180
acggagggga ggagcaggag acaggggga agcacctccc acgactttgg caggccgaac     240
cgaacgccac aaaagtagga tttttctccg gttccccggg aacagtcttt ttcttctact     300
ggcagaaacg gacggttcag gtgcgggagc ttccggctg ctgctgctgc cgccggcctt     360
tttgcgatac catactgggg gtttggcccc gggaatgctg gattgggttt tgttcgtggt     420
actcttggtt tcggactca tcacctggta atgtcgctat cgggtggatg gatctcggcg     480
acgcgagacg tacactgatt tcttttctt ttttctttat caatcagtta tcagtacgta     540
ctgctaccta gggtcctctc ttttttttcc ccggatgcaa aatacgtact gcctgtaacc     600
aatattatat ttatatagat aaaaacaaca taaattttaa gtccctatgt ttatctgaaa     660
atttagaaca gcaatagtca tttcagtgga ccaaaggatt gggttagaat ctggacagtg     720
attgcgggag aagtcctgcc atgagcttag ggtcctagtt tggcaactcc atctttctaa     780
ggccttgttc gtttgtgtcg gattacaccc gaaatcgtta cagctaatca agtttatat     840 aaattagaga agcaatccgg ataggaatcg ttccgaccca ccaatccgcc acaaacgaac     900
aaggcctaaa gattttcatc tttccaaaga aaaataaact aaactttctt ggaaaaaaat     960
ataaatctct taaaaatgt ggttgccaaa ctagcccta taataaagga aaaactggag    1020 gaatttaga ggaatgaaat cctatatgaa attatgttat gtggccttg aaacagaggc    1080 tttagttcct acatatccta taaggttcct atggaatggt ccatcgtagt gatattttag    1140
agaatttcta acttaaagcc cgacctctta gaaattgtca tttgtgcctc tctctctgca    1200
ctctaattca tgtgttcttt ctatgttgca tccaggattc tcaaaacacg gaaataggag    1260
aaacacatga ttataacgcc catgccgttg aaatcctaca aaaatttata acacggaaaa    1320
gttataaaaa catgttttg gatcatgcgc ataaaaaata taggaatgtg agacacaaag    1380
aaaataaaat atgagggtgg acctcacgct taatttccc tccaaaatta ccatggagca    1440
tgtcatttca taggattttt caaggaattg ataggatcca atcatttgtc ccaaaaggct    1500
```

-continued

```
tttatatgaa aactttctat gcgaattgaa tcctctaaag ttcctttgtt tttcctccat    1560
tccaaagtta tctgcgtttt taattcatgt atgattacaa gtgttataca actctattcg    1620
tacatttttt ttcctttcta tttttgtatt ttgtcaatcc tctgttccaa aggaggcatc    1680
taaaataggg aatgagatag ccttaatcga gtactagtag catttgatat atcataaaaa    1740
agtagcattt gatatgtgcg agaagagctg gggttaacgt cgtaacgcaa atagttaact    1800
agacggaaac cggtagcgga aacaaaatca gccttgtggc cgcaactaca ccaaatagca    1860
ccatcaagtc actatcgaaa tcgccctgtt gcctccctac ttgcaagctg gaagctgcaa    1920
cttgcgtccc cgtccagccg tccttgctct ctgacccaga tgcagccccc ttccttcccc    1980
agtgcctggt ggctcccctc ccgcgttatt cactctgcta gtcctgctca ggtctgctga    2040
ctgctgctct ctgatccaaa cctcctcctc caccaccacc tataaatacg catcctcaaa    2100
tccaccattc ccaaatcgaa aaccactcga acacaagctc aggcaaggca aaaggaaccc    2160
gcaccatccg aggctcaagc agagaagtga tcatcatcat cagaagaaga tgtgcccaac    2220
caagaagggg atgaccggag agccgagctc gccatgcagc tcggca                  2266
```

US 8,088,977 B2

REGULATORY ELEMENTS ASSOCIATED WITH CBF TRANSCRIPTION FACTORS OF MAIZE

CROSS REFERENCE

This utility application claims the benefit of U.S. Provisional Application No. 60/971,278, filed Sep. 11, 2007, which is incorporated herein by reference.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of operably linked regulatory elements that are functional within the plant host. Choice of the regulatory element will determine when and where within the organism the heterologous DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs is desired, tissue-specific or tissue-preferred promoters may be used to drive expression preferentially in certain tissues or organs. Such tissue-specific or tissue-preferred promoters may be temporally constitutive or inducible. In either case, additional regulatory sequences upstream and/or downstream from a core promoter sequence may be included in expression constructs of transformation vectors to bring about varying levels of expression of heterologous nucleotide sequences in a transgenic plant.

As this field develops and more genes become accessible, a greater need exists for transformed plants with multiple genes, and these multiple exogenous genes typically need to be controlled by separate regulatory sequences. Further, some genes should be regulated constitutively, whereas other genes should be expressed at certain developmental stages or locations in the transgenic organism. Accordingly, a variety of regulatory sequences having diverse effects is needed.

Diverse regulatory sequences are also needed as undesirable biochemical interactions can result from using the same regulatory sequence to control more than one gene. For example, transformation with multiple copies of a regulatory element may cause problems, such that expression of one or more genes may be adversely affected.

Transgenic modulation of early sensing and signaling genes involved in abiotic stress responses requires expression of the transgenes early upon exposure to the stress and at a moderate level. Also, expression of such transgenes needs to be turned off at later stages of stress exposure so as to avoid the continued induction of downstream targets, a scenario which can easily lead to yield penalty. The current invention provides two regulatory sequences which can be used for early expression and tight modulation of signaling and sensing genes, for transgenic modulation of plant stress tolerance.

The inventors herein disclose the isolation and characterization of promoters associated with stress-related transcription factors that can serve as regulatory elements for expression of isolated nucleotide sequences of interest, thereby impacting various traits in plants. Alternatively or additionally, the promoters may be used to drive scorable markers.

SUMMARY OF THE INVENTION

The invention provides plant promoters which regulate transcription and are induced in response to abiotic stress.

In an embodiment, the promoter drives transcription in a stress-responsive manner, wherein said promoter comprises a nucleotide sequence selected from the group consisting of:

a) sequences natively associated with, and that regulate expression of, DNA coding for the CBF1 or CBF2 transcription factor in maize (*Zea mays*);

b) the nucleotide sequence set forth in SEQ ID NO: 1 or SEQ ID NO: 2; and c) a sequence comprising a fragment of the nucleotide sequence set forth in SEQ ID NO: 1 or SEQ ID NO: 2.

Further embodiments are to expression cassettes, transformation vectors, plants, plant cells and plant parts comprising the above nucleotide sequences. The invention is further to methods of using the sequence in plants and plant cells. An embodiment of the invention further comprises the nucleotide sequences described above operably linked to a detectable marker.

BRIEF DESCRIPTION OF THE FIGURES

FIG. 1 shows the regulatory sequence of ZmCBF1 (1329 base pairs). Putative cis-acting elements, including a TATA box (bold), CRT/DRE consensus sequence (boxed with double lines), ABRE core motif (single underline), and myc-binding sequences (boxed with single lines) are marked. Bold letters, double underline and an arrow indicate the translation start site, ATG. All features are also indicated in the sequence listing at SEQ ID NO: 1.

FIG. 2 shows the regulatory sequence of ZmCBF2 (2209 base pairs). Putative cis-acting elements, including a TATA box (bold), CRT/DRE consensus sequence (boxed with double lines), and myc-binding sequences (boxed with single line) are marked. A putative transcription start site is indicated by a double underline. Bold letters, double underline and an arrow indicate the translation start site, ATG. All features are also indicated in the sequence listing at SEQ ID NO: 2.

DETAILED DESCRIPTION OF THE INVENTION

All public disclosures referred to herein are incorporated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Plants adapt to environmental stresses such as cold, drought, and salinity through modulation of gene expression. Promoter regions of stress-inducible genes may comprise cis-acting elements, which are DNA fragments recognized by trans-acting factors. Transacting factors include plant hormones such as abscisic acid (ABA) which has been shown to bind to an ABA-responsive element (ABRE); see, for example, Yamaguchi-Shinozaki, et al., (2005) *Trends in Plant Science* 10(2):88-94. Other transacting factors include nuclear proteins capable of binding to regulatory DNA and interacting with other molecules, notably DNA Polymerase III, to initiate transcription of DNA operably linked to said regulatory DNA. These transcription factors may exist as families of related proteins that share a DNA-binding domain. The transcription factor genes may themselves be induced by stress. Furthermore, the downstream targets of cis-regulated genes may be transcription factors, creating a complex network of gene response cascades.

DRE/CRT (Dehydration Response Element/C-Repeat) cis elements function in response to stress and have been identified in numerous plant species, including *Arabidopsis*, barley, *Brassica*, citrus, cotton, eucalyptus, grape, maize, melon, pepper, rice, soy, tobacco, tomato and wheat. The DRE/CRT elements comprise a core binding site, A/GCCGAC, recognized by the trans-activating factors known as DREB1 (DRE-Binding) and CBF (C-Repeat Binding Factor). Secondary structure in proximity to the cis element, and/or multiple cis factors, appear to be additional components necessary for stress-inducible expression. (For reviews see, Agarwal, et al., (2006) *Plant Cell Rep* 25:1263-1274; Yamaguchi-Shinozaki and Shinozaki (2005) *Trends in Plant Science* 10(2):88-94.) The promoter regions of the CBF/DREB genes may comprise cis-acting elements such as ICEr1 and ICEr2 (Zarka, et al., (2003) *Plant Physiol.* 133:910-918; Massari and Murre (2000) *Mol. Cell. Bio.* 20:429-440).

Other transcription factors include the MYC and MYC-like proteins (see, for example, Zhu, et al., (2003) *J. Biol. Chem.* 278(48):47803-47811).

In accordance with the invention, nucleotide sequences are provided that allow regulation of transcription in response to stress. The sequences of the invention comprise regulatory elements associated with stress-responsive polynucleotides. Thus, the compositions of the present invention comprise novel nucleotide sequences for plant regulatory elements natively associated with the nucleotide sequences coding for ZmCBF1 and ZmCBF2.

ZmCBF1 and ZmCBF2 belong to the DREB1 class of transcription factors which are induced early upon exposure to abiotic stresses such as cold, drought, and salt. The promoter of the *Arabidopsis* CBF3 gene is known to contain five myc-binding sites and to bind to a basic helix-loop-helix protein known as the ICE1 (inducer of CBF expression) which is an upstream regulatory protein of CBF. A DREB1B promoter from rice (GenBank EF556551) has been isolated by Gutha and Reddy, and was shown to be induced by abiotic stress. (Plant Molecular Biology online 10.1007/s11103-008-9391-8, 28 Aug. 2008). Badawi, et al., (Plant Cell Physiol. 49(8):1237-1249 (2008)) reported an analysis of wheat ICE (inducer of DREB1/CBF expression) genes and their impact on expression of cold-regulated genes of *Arabidopsis*.

Identification of the regulatory regions of ZmCBF1 and ZmCBF2 will (a) allow their use for low-level expression and tight modulation of early sensing and signaling genes, and (b) help to identify the maize orthologs of ICE1 transcription factor either by yeast one-hybrid screen or to confirm the function of maize orthologs identified by sequence homology using electrophoretic mobility shift assays. ZmCBF1 and ZmCBF2 were previously published; see, U.S. Pat. Nos. 7,253,000 and 7,317,141. As documented in Example 4 of U.S. Pat. No. 7,317,141, endogenous ZmCBF2 is rapidly induced by cold stress. Similar work with ZmCBF1 has shown that it too is inducible by cold, with peak expression at 4 hours after imposition of cold stress. ZmCBF1 has also been evaluated for expression under drought stress; it is induced within 24 hours of the withholding of water, with peak expression at 27 hours. In case of gene expression under cold, induced levels decreased after the peak and returned to zero upon recovery from cold over a period of 48 hours. In case of gene expression under drought, induced levels gradually declined after the peak expression and returned to zero after about 36 hours of withholding water. In both tests, no ZmCBF1 expression was observed prior to the stress treatment. Stress-induced endogenous expression is consistent with the identification of stress-responsive elements within the ZmCBF promoter sequences as described elsewhere herein.

The ZmCBF regulatory element will be operably linked to a sequence of interest, regulating initiation of transcription of the operably-linked polynucleotide, which will provide for modification of the phenotype of the plant. Such initiation of transcription may be referred to as "promoter activity." Such modification includes modulating the production of an endogenous product, as to amount, relative distribution, or the like, or production of an exogenous expression product to provide for a novel function or product. For example, such a promoter is useful for modulation of expression of sequences encoding stress-responsive proteins, including other transcription factors. Additionally, linking a stress-induced promoter with a marker, and, in particular, a visual marker, may be useful in tracking the expression of a linked gene of interest.

A method for expressing an isolated nucleotide sequence in a plant using a regulatory sequence disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a stress-induced manner.

Frequently it is desirable to have preferential expression of a DNA sequence in a tissue of an organism, or under certain environmental conditions. For example, increased resistance of a plant to insect attack might be accomplished by genetic manipulation of the plant's genome to comprise a tissue-specific promoter operably linked to a heterologous insecticide gene such that the insect-deterring substances are specifically expressed in the susceptible plant tissues. Increased tolerance to abiotic stress might be accomplished by genetic manipulation of the plant's genome to comprise a stress-induced promoter operably linked to a heterologous gene encoding a plant hormone such that the hormone is specifically expressed under the stress conditions. Preferential expression of the heterologous nucleotide sequence in the appropriate tissue or under the appropriate conditions reduces the drain on the plant's resources that occurs when a constitutive promoter initiates transcription of a heterologous nucleotide sequence throughout the cells of the plant.

Alternatively, it might be desirable to inhibit expression of a native DNA sequence within a plant's tissues to achieve a desired phenotype. For example, a hairpin configuration comprising all or a portion of the respective ZmCBF promoter may be used to downregulate the native stress-responsive CBF1 or CBF2, or to downregulate any other coding region to which the ZmCBF promoter is linked. When such downregulation of a stress-responsive polynucleotide is appropriately targeted, for example with a reproductive-tissue-preferred promoter, certain plant tissues may avoid detrimental effects of stress. In another example, the ZmCBF promoter is operably linked to an antisense nucleotide sequence, such that stress-induced expression of the antisense sequence produces an RNA transcript that interferes with translation of the mRNA of a second DNA sequence in a subset of the plant's cells.

DEFINITIONS

For the purposes of the present invention, unless indicated otherwise or apparent from the context, a "subject plant" or "subject plant cell" is one in which genetic alteration, such as transformation, has been effected as to a gene of interest, or is a plant or plant cell which is descended from a plant or plant cell so altered and which comprises the alteration. A "control" or "control plant" or "control plant cell" provides a reference point for measuring changes in the subject plant or plant cell.

A control plant or control plant cell may comprise, for example: (a) a wild-type plant or plant cell, i.e., of the same genotype as the starting material for the genetic alteration which resulted in the subject plant or subject plant cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or subject plant cell; (d) a plant or plant cell genetically identical to the subject plant or subject plant cell but which is not exposed to conditions or stimuli that would induce expression of the gene of interest; or (e) the subject plant or subject plant cell itself, under conditions in which the gene of interest is not expressed.

By "stress-induced" is intended favored expression under conditions of stress to the plant, particularly abiotic stress, for example conditions of drought, cold, high temperature, or high salinity.

By "regulatory element" is intended sequences responsible for expression of the associated coding sequence including, but not limited to, promoters, terminators, enhancers, introns, and the like.

By "terminator" is intended a regulatory region of DNA that causes RNA polymerase to disassociate from DNA, causing termination of transcription.

By "promoter" is intended a regulatory region of DNA capable of regulating the transcription of a sequence linked thereto, i.e., a region of DNA having promoter activity. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein may comprise upstream regulatory elements such as those responsible for tissue and temporal expression of the coding sequence, and may include enhancers, the DNA response element for a transcriptional regulatory protein, ribosomal binding sites, transcriptional start and stop sequences, translational start and stop sequences, activator sequence and the like.

In the same manner, the promoter elements which enable expression under stress conditions can be identified, isolated, and used with other core promoters. By core promoter is meant the minimal sequence required to initiate transcription, such as the sequence called the TATA box which is common to promoters in genes encoding proteins. Thus the upstream promoter of ZmCBF1 or ZmCBF2 can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive stress-induced expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon. The term "isolated" refers to material, such as a nucleic acid or protein, which is: (1) substantially or essentially free from components which normally accompany or interact with the material as found in its naturally occurring environment; or (2) if the material is in its natural environment, the material has been altered by deliberate human intervention to a composition and/or placed at a locus in a cell other than the locus native to the material. Methods for isolation of promoter regions are well known in the art.

The complete genomic sequence for maize ZmCBF1 gene has been previously published (US Patent Application Publication Number 2006/0162027). The maize CBF1 promoter is set forth in SEQ ID NO: 1 and is 1373 nucleotides in length. The maize CBF2 promoter is set forth in SEQ ID NO: 2 and is 2266 nucleotides in length.

Motifs identified in the ZmCBF1 or ZmCBF2 promoter are shown in FIG. 1 and in the sequence listing.

The promoter regions of the invention may be isolated from any plant, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa and sorghum.

Promoter sequences from other plants may be isolated according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e., genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions and which drive expression of an operably-linked sequence under conditions similar to those under which the native promoter is active. Functional variants of the invention may be created by site-directed mutagenesis or by induced mutation, or may occur as allelic variants (polymorphisms).

As used herein, a "functional fragment" is a truncated regulatory sequence formed by one or more deletions from a larger regulatory element. For example, the 5' portion of a promoter up to the TATA box near the transcription start site can be deleted without abolishing promoter activity, as described by Opsahl-Sorteberg, H-G., et al., (2004) "Identification of a 49-bp fragment of the HvLTP2 promoter directing aleruone cell specific expression" *Gene* 341:49-58. Such fragments should retain promoter activity, particularly the ability to drive stress-induced expression. Activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis, et al., (1987) *Methods Enzymol.* 155:335-350, and Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3',4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see, e.g., Innis, et al., (1990) *PCR Protocols, A Guide to Methods and Applications*, eds., Academic Press).

The stress-induced regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a promoter and a second sequence, wherein the promoter sequence initiates and mediates transcription of the DNA sequence corresponding to the second sequence. The expression cassette will include a regulatory sequence of the invention operably linked to at least one sequence of interest.

In one typical embodiment, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994 herein incorporated in its entirety by reference.

The regulatory elements of the invention can be operably linked in expression cassettes along with isolated polynucleotide sequences of interest for expression in the plant. Such an expression cassette is provided with a plurality of restriction sites for insertion of the nucleotide sequence of interest under the transcriptional control of the regulatory elements.

The regulatory elements of the invention can be used for directing expression of a sequence in plant tissues. This can be achieved by increasing expression of endogenous or exogenous products. Alternatively, the results can be achieved by providing for a reduction of expression of one or more endogenous products, particularly enzymes or cofactors. This down regulation can be achieved through many different approaches known to one skilled in the art, including antisense, cosuppression, use of hairpin formations, or others, and discussed infra. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms.

Modifications that affect grain traits include increasing the content of oleic acid, or altering levels of saturated and unsaturated fatty acids. Likewise, the level of proteins, particularly modified proteins that improve the nutrient value of the plant, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997. Another example is lysine and/or sulfur-rich root protein encoded by the soybean 2S albumin described in WO 9735023 filed Mar. 20, 1996, and the chymotrypsin inhibitor from barley, Williamson, et al., (1987) *Eur. J. Biochem.* 165: 99-106.

Agronomic traits can be improved by altering expression of genes that affect the response of root, plant or seed growth and development during environmental stress, Cheikh-N, et al., (1994) *Plant Physiol.* 106(1):45-51, and genes controlling carbohydrate metabolism to reduce kernel abortion in maize, Zinselmeier, et al., (1995) *Plant Physiol.* 107(2):385-391.

It is recognized that any gene of interest, including the native coding sequence, can be operably linked to the regulatory elements of the invention and expressed in the plant.

By way of illustration, without intending to be limiting, are examples of the types of genes which can be used in connection with the regulatory sequences of the invention.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (Arabidopsis RSP2 gene for resistance to *Pseudomonas syringae*); McDowell and Woffenden, (2003) *Trends Biotechnol.* 21(4):178-83 and Toyoda, et al., (2002) *Transgenic Res.* 11 (6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; PCT Application Numbers WO 91/14778; WO 99/31248; WO 01/12731; WO 99/24581; WO 97/40162 and U.S. patent application Ser. Nos. 10/032,717; 10/414,637 and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone.

(D) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853; and Vasconcelos and Oliveira (2004) *Toxicon* 44(4):385-403. See also, U.S. Pat. No. 5,266,317 to Tomalski, et al., who disclose genes encoding insect-specific toxins.

(E) An enzyme responsible for a hyperaccumulation of a monoterpene, a sesquiterpene, a steroid, hydroxycinnamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase or a glucanase, whether natural or synthetic. See, PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase; and Kawalleck, et al., (1993) *Plant Molec. Biol.* 21:673, who provide the nucleotide sequence of the parsley ubi4-2 polyubiquitin gene; U.S. application Ser. Nos. 10/389,432, 10/692,367 and U.S. Pat. No. 6,563,020.

(G) A molecule that stimulates signal transduction. For example, see the disclosure by Botella, et al., (1994) *Plant Molec. Biol.* 24:757, of nucleotide sequences for mung bean calmodulin cDNA clones; and Griess, et al., (1994) *Plant Physiol.* 104:1467, who provide the nucleotide sequence of a maize calmodulin cDNA clone.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf., Taylor, et al., Abstract #497, *Seventh Int'l Symposium on Molecular Plant-microbe Interactions* (Edinburgh, Scotland, 1994) (enzymatic inactivation in transgenic tobacco via production of single-chain antibody fragments).

(L) A virus-specific antibody. See, for example, Tavladoraki, et al. (1993), *Nature* 366:469, who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology*, 5(2):128-131; Pieterse and Van Loon (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712; Parijs, et al., (1991) *Planta* 183:258-264; and Bushnell, et al., (1998) *Can. J. of Plant Path.* 20(2):137-149. Also see, U.S. patent application Ser. No. 09/950,933.

(Q) Detoxification genes, such as for fumonisin, beauvericin, moniliformin and zearalenone and their structurally related derivatives. For example, see, U.S. Pat. No. 5,792,931.

(R) Cystatin and cysteine proteinase inhibitors. See, U.S. patent application Ser. No. 10/947,979.

(S) Defensin genes. See, PCT Application Number WO 03/000863 and U.S. patent application Ser. No. 10/178,213.

(T) Genes conferring resistance to nematodes. See, PCT Application Number WO 03/033651 and Urwin, et al., (1998) *Planta* 204:472-479; Williamson (1999) *Curr Opin Plant Bio.* 2(4):327-31.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035.

2. Transgenes that Confer Resistance to a Herbicide Such as:

(A) An herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241; and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; and PCT Application Number WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; Re. 36,449; RE 37,287 E and 5,491,288; and international publication numbers EP1173580; WO 01/66704; EP1173581 and EP1173582. Glyphosate resistance is also imparted to plants that express a gene that encodes a glyphosate oxido-reductase enzyme as described more fully in U.S. Pat. Nos. 5,776,760 and 5,463,175. In addition glyphosate resistance can be imparted to plants by the over expression of genes encoding glyphosate N-acetyltransferase. See, for example, U.S. patent application Ser. No. 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European Patent Number 0 242 246 and 0 242 236 to Leemans, et al. De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903. Exemplary genes conferring resistance to phenoxy proprionic acids and cycloshexones, such as sethoxydim and haloxyfop, are the Acc1-S1, Acc1-S2 and Acc1-S3 genes described by Marshall, et al., (1992) *Theor. Appl. Genet.* 83:435.

(C) A herbicide that inhibits photosynthesis, such as a triazine (psbA and gs+ genes) and a benzonitrile (nitrilase gene). Przibilla, et al., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173.

(D) Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106:17), genes for glutathione reductase and superoxide dismutase (Aono, et al., (1995) *Plant Cell Physiol* 36:1687, and genes for various phosphotransferases (Datta, et al., (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837 and 5,767,373; and international publication number WO 01/12825.

3. Transgenes That Confer pr Contribute To an Altered Grain Characteristic, Such As:
   (A) Altered fatty acids, for example, by
      (1) Down-regulation of stearoyl-ACP desaturase to increase stearic acid content of the plant. See, Knultzon, et al., (1992) *Proc. Natl. Acad. Sci. USA* 89:2624 and PCT Application Number WO 99/64579 (Genes for Desaturases to Alter Lipid Profiles in Corn),
      (2) Elevating oleic acid via FAD-2 gene modification and/or decreasing linolenic acid via FAD-3 gene modification (see, U.S. Pat. Nos. 6,063,947; 6,323,392; 6,372,965 and PCT Application Number WO 93/11245),
      (3) Altering conjugated linolenic or linoleic acid content, such as in PCT application Number WO 01/12800,
      (4) Altering LEC1, AGP, Dek1, Superal1, milps, various Ipa genes such as Ipa1, Ipa3, hpt or hggt. For example, see, PCT Application Numbers WO 02/42424, WO 98/22604, WO 03/011015, U.S. Pat. No. 6,423,886, U.S. Pat. No. 6,197,561, U.S. Pat. No. 6,825,397, US Patent Application Publication Number 2003/0079247, US Patent Application Publication Number 2003/0204870, PCT Application Numbers WO 02/057439, WO 03/011015 and Rivera-Madrid, et. al., (1995) *Proc. Natl. Acad. Sci.* 92:5620-5624.
   (B) Altered phosphorus content, for example, by the
      (1) Introduction of a phytase-encoding gene. This would enhance breakdown of phytate, adding more free phosphate to the transformed plant.
   For example, see, Van Hartingsveldt, et al., (1993) *Gene* 127:87, for a disclosure of the nucleotide sequence of an *Aspergillus niger* phytase gene.
      (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in PCT Application Number WO 02/059324, US Patent Application Publication Number 2003/0009011, PCT Application Number WO 03/027243, US Patent Application Publication Number 2003/0079247, PCT Application Number WO 99/05298, U.S. Pat. No. 6,197,561, U.S. Pat. No. 6,291,224, U.S. Pat. No. 6,391,348, PCT Application Number WO 2002/059324, US Patent Application Publication Number 2003/0079247, PCT Application Numbers WO 98/45448, WO 99/55882, WO 01/04147.

(C) Altered carbohydrates effected, for example, by altering a gene for an enzyme that affects the branching pattern of starch or a gene altering thioredoxin. (See, U.S. Pat. No. 6,531,648). See, Shiroza, et al., (1988) *J. Bacteriol.* 170:810 (nucleotide sequence of *Streptococcus mutans* fructosyltransferase gene); Steinmetz, et al., (1985) *Mol. Gen. Genet.* 200:220 (nucleotide sequence of *Bacillus subtilis* levansucrase gene); Pen, et al., (1992) *Bio/Technology* 10:292 (production of transgenic plants that express *Bacillus licheniformis* alpha-amylase); Elliot, et al., (1993) *Plant Molec. Biol.* 21 515 (nucleotide sequences of tomato invertase genes); Søgaard, et al., (1993) *J. Biol. Chem.* 268:22480 (site-directed mutagenesis of barley alpha-amylase gene); and Fisher, et al., (1993) *Plant Physiol.* 102:1045 (maize endosperm starch branching enzyme II), WO Application Number 99/10498 (improved digestibility and/or starch extraction through modification of UDP-D-xylose 4-epimerase, Fragile 1 and 2, Refl, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and PCT Application Number WO 00/68393 involving the manipulation of antioxidant levels through alteration of a phytl prenyl transferase (ppt), WO Application Number 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), PCT Application Number WO 99/40209 (alteration of amino acid compositions in seeds), PCT Application Number WO 99/29882 (methods for altering amino acid content of proteins), U.S. Pat. No. 5,850,016 (alteration of amino acid compositions in seeds), PCT Application Number WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), PCT Application Number WO 98/56935 (plant amino acid biosynthetic enzymes), PCT Application Number WO 98/45458 (engineered seed protein having higher percentage of essential amino acids), PCT Application Number WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), PCT Application Number WO 96/01905 (increased threonine), PCT Application Number WO 95/15392 (increased lysine), US Patent Application Publication Number 2003/0163838, US Patent Application Publication Number 2003/0150014, US Patent Application Publication Number 2004/0068767, U.S. Pat. No. 6,803,498, PCT Application Number WO 01/79516, and PCT Application Number WO 00/09706 (Ces A: cellulose synthase), U.S. Pat. No. 6,194,638 (hemicellulose), U.S. Pat.

No. 6,399,859 and US Patent Application Publication Number 2004/0025203 (UDPGdH), U.S. Pat. No. 6,194,638 (RGP).

4. Genes that Control Male-sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (PCT Application Number WO 01/29237).

(B) Introduction of various stamen-specific promoters (PCT Application Numbers WO 92/13956, WO 92/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. No. 5,859,341; 6,297,426; 5,478,369; 5,824,524; 5,850,014; and 6,265,640.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants" *Plant Cell Rep* 21:925-932 and PCT Application Number WO 99/25821, which are hereby incorporated by reference. Other systems that may be used include the Gin recombinase of phage Mu (Maeser, et al., (1991) *Mol Gen Genet.* 230(1-2):170-6); Vicki Chandler, *The Maize Handbook* ch. 118 (Springer-Verlag 1994), the Pin recombinase of *E. coli* (Enomoto, et al., 1983) and the R/RS system of the pSR1 plasmid (Araki, et al., (1992) *J Mol. Biol.* 225(1):25-37).

6. Genes that Affect Abiotic Stress Resistance (including but not limited to modulation of flowering, ear and seed development, enhancement of nitrogen utilization efficiency, altered nitrogen responsiveness, drought resistance or tolerance, cold resistance or tolerance, and salt resistance or tolerance) and increased yield under stress.

For example, see, PCT Application Number WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, PCT Application Numbers WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521 and WO 99/38977 describing genes, including CBF genes and transcription factors effective in mitigating the negative effects of freezing, high salinity, and drought on plants, as well as conferring other positive effects on plant phenotype; US Patent Application Publication Number 2004/0148654 and PCT Application Number WO 01/36596 where abscisic acid is altered in plants resulting in improved plant phenotype such as increased yield and/or increased tolerance to abiotic stress; PCT Application Numbers WO 2000/006341, WO 04/090143, U.S. patent application Ser. Nos. 10/817,483 and 09/545,334 where cytokinin expression is modified resulting in plants with increased stress tolerance, such as drought tolerance, and/or increased yield. Also see, PCT Application Numbers WO 02/02776, WO 2003/052063, JP 2002281975, U.S. Pat. No. 6,084,153, PCT Application Number WO 0164898, U.S. Pat. Nos. 6,177,275 and 6,107,547 (enhancement of nitrogen utilization and altered nitrogen responsiveness). For ethylene alteration, see, US Patent Application Publication Number 2004/0128719, US Patent Application Publication Number 2003/0166197 and PCT Application Number WO 2000/32761. For plant transcription factors or transcriptional regulators of abiotic stress, see, e.g., US Patent Application Publication Number 2004/0098764 or US Patent Application Publication Number 2004/0078852.

Other genes and transcription factors that affect plant growth and agronomic traits such as yield, flowering, plant growth and/or plant structure, nutrient uptake, especially nitrogen uptake by plants, nitrogen use efficiency; drought tolerance and water use efficiency; root strength, and root lodging resistance; soil pest management, corn root worm resistance can be introduced or introgressed into plants, see e.g., PCT Application Numbers WO 97/49811 (LHY), WO 98/56918 (ESD4), WO 97/10339 and U.S. Pat. No. 6,573,430 (TFL), U.S. Pat. No. 6,713,663 (FT), PCT Application Numbers WO 96/14414 (CON), WO 96/38560, WO 01/21822 (VRN1), WO 00/44918 (VRN2), WO 99/49064 (GI), WO 00/46358 (FRI), WO 97/29123, U.S. Pat. Nos. 6,794,560, 6,307,126 (GAI), PCT Application Numbers WO 99/09174 (D8 and Rht), and WO 2004/076638 and WO 2004/031349 (transcription factors).

Commercial traits in plants can be created through the expression of genes that alter starch or protein for the production of paper, textiles, ethanol, polymers or other materials with industrial uses.

Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering (see, Nobrega, et. al., (2004) *Nature* 431:988-993), homologous recombination, TILLING (Targeting Induced Local Lesions In Genomes; McCallum, et al., (2000) *Nature Biotechnol.* 18:455-457), and biosynthetic competition to manipulate the expression of proteins.

Many techniques for gene silencing are well known to one of skill in the art, including but not limited to knock-outs such as by insertion of a transposable element such as Mu, Vicki Chandler, *The Maize Handbook* ch. 118 (Springer-Verlag 1994) or other genetic elements such as a FRT, Lox or other site specific integration site; RNA interference (Napoli, et al., (1990) *Plant Cell* 2:279-289; U.S. Pat. No. 5,034,323, Sharp (1999) *Genes Dev.* 13:139-141, Zamore, et al., (2000) *Cell* 101:25-33; and Montgomery, et al., (1998) *PNAS USA* 95:15502-15507); virus-induced gene silencing (Burton, et al., (2000) *Plant Cell* 12:691-705, and Baulcombe (1999) *Curr. Op. Plant Bio.* 2:109-113); target-RNA-specific ribozymes (Haseloff, et al., (1988) *Nature* 334:585-591); hairpin structures (Smith, et al., (2000) *Nature* 407:319-320;

PCT Application Numbers WO 99/53050; and WO 98/53083); MicroRNA (Aukerman and Sakai (2003) *Plant Cell* 15:2730-2741); ribozymes (Steinecke, et al., (1992) *EMBO J.* 11:1525, and Perriman, et al., (1993) *Antisense Res. Dev.* 3:253); oligonucleotide mediated targeted modification (e.g., PCT Application Numbers WO 03/076574 and WO 99/25853); zinc-finger targeted molecules (e.g., PCT Application Numbers WO 01/52620; WO 03/048345; and WO 00/42219); and other methods or combinations of the above methods known to those of skill in the art.

Any method of increasing or inhibiting a protein can be used in the present invention. Several examples are outlined in more detail below for illustrative purposes.

The nucleotide sequence operably linked to the regulatory elements disclosed herein can be an antisense sequence for a targeted gene. (See, e.g., Sheehy, et al., (1988) *PNAS USA* 85:8805-8809; and U.S. Pat. Nos. 5,107,065; 5,453,566 and 5,759,829). By "antisense sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant.

As noted, other potential approaches to impact expression of proteins in the plant include traditional co-suppression, that is, inhibition of expression of an endogenous gene through the expression of an identical structural gene or gene fragment introduced through transformation (Goring, et al., (1991) *Proc. Natl. Acad. Sci. USA* 88:1770-1774 co-suppression; Taylor (1997) *Plant Cell* 9:1245; Jorgensen (1990) *Trends Biotech.* 8(12):340-344; Flavell (1994) *PNAS USA* 91:3490-3496; Finnegan, et al., (1994) *Bio/Technology* 12:883-888; and Neuhuber, et al., (1994) *Mol. Gen. Genet.* 244:230-241). In one example, co-suppression can be achieved by linking the promoter to a DNA segment such that transcripts of the segment are produced in the sense orientation and where the transcripts have at least 65% sequence identity to transcripts of the endogenous gene of interest, thereby suppressing expression of the endogenous gene in said plant cell. (See, U.S. Pat. No. 5,283,184). The endogenous gene targeted for co-suppression may be a gene encoding any protein that accumulates in the plant species of interest. For example, where the endogenous gene targeted for co-suppression is the 50 kD gamma-zein gene, co-suppression is achieved using an expression cassette comprising the 50 kD gamma-zein gene sequence, or variant or fragment thereof.

Additional methods of suppression are known in the art and can be similarly applied to the instant invention. These methods involve the silencing of a targeted gene by spliced hairpin RNA's and similar methods also called RNA interference and promoter silencing (see, Smith, et al., (2000) *Nature* 407:319-320, Waterhouse and Helliwell (2003) *Nat. Rev. Genet.* 4:29-38; Waterhouse, et al., (1998) *Proc. Natl. Acad. Sci. USA* 95:13959-13964; Chuang and Meyerowitz (2000) *Proc. Natl. Acad. Sci. USA* 97:4985-4990; Stoutjesdijk, et al., (2002) *Plant Phystiol.* 129:1723-1731; and PCT Application Numbers WO 99/53050; WO 99/49029; WO 99/61631; WO 00/49035 and U.S. Pat. No. 6,506,559).

For miRNA interference, the expression cassette is designed to express an RNA molecule that is modeled on an endogenous gene. The miRNA molecule encodes an RNA that forms a hairpin structure containing a 22-nucleotide sequence that is complementary to the endogenous gene (target sequence). miRNA molecules are highly efficient at inhibiting the expression of endogenous genes, and the RNA interference they induce is inherited by subsequent generations of plants.

In one embodiment, the polynucleotide to be introduced into the plant comprises an inhibitory sequence that encodes a zinc finger protein that binds to a gene resulting in reduced expression of the gene. In particular embodiments, the zinc finger protein binds to a regulatory region of the invention. In other embodiments, the zinc finger protein binds to a messenger RNA encoding a protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355.

The expression cassette may also include, at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

Any convenient termination regions can be used in conjunction with the promoter of the invention, and are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; Joshi, et al., (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein, et al., (1989) *Proc. Natl. Acad. Sci. USA* 86:6126-6130; potyvirus leaders, for example, TEV leader (Tobacco Etch Virus), Allison, et al., (1986) "The Nucleotide Sequence of the Coding Region of Tobacco Etch Virus Genomic RNA: Evidence for the Synthesis of a Single Polyprotein", *Virology* 154:9-20; MDMV leader (Maize Dwarf Mosaic Virus); human immunoglobulin heavy-chain binding protein (BiP), Macejak, et al., (1991) *Nature* 353:90-94; untranslated leader from the coat protein mRNA of alfalfa mosaic virus (AMV RNA 4), Jobling, et al., (1987) *Nature* 325:622-625); tobacco mosaic virus leader (TMV), Gallie, et al., (1989) *Molecular Biology of RNA*, pages 237-256; and maize chlorotic mottle virus leader (MCMV), Lommel, et al., (1991) *Virology* 81:382-385. See also, Della-Cioppa, et al., (1987) *Plant Physiology* 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments, or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements of the invention. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook, et al. (supra).

The transformation vector, comprising the regulatory sequences of the present invention operably linked to an isolated polynucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At a minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example, Jefferson, et al., (1991) in *Plant Molecular Biology Manual*, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *BioTechniques* 19:650-655; and Chiu, et al., (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella, et al., (1983) *EMBO J.* 2:987-992; methotrexate, Herrera Estrella, et al., (1983) *Nature* 303:209-213; Meijer, et al., (1991) *Plant Mol. Biol.* 16:807-820; hygromycin, Waldron, et al., (1985) *Plant Mol. Biol.* 5:103-108; Zhijian, et al., (1995) *Plant Science* 108:219-227; streptomycin, Jones, et al., (1987) *Mol. Gen. Genet.* 210:86-91; spectinomycin, Bretagne-Sagnard, et al., (1996) *Transgenic Res.* 5:131-137; bleomycin, Hille, et al., (1990) *Plant Mol. Biol.* 7:171-176; sulfonamide, Guerineau, et al., (1990) *Plant Mol. Biol.* 15:127-136; bromoxynil, Stalker, et al., (1988) *Science* 242:419-423; glyphosate, Shaw, et al., (1986) *Science* 233:478-481; phosphinothricin, DeBlock, et al., (1987) *EMBO J.* 6:2513-2518.

Further, when linking a promoter of the invention with a nucleotide sequence encoding a detectable protein, stress-induced expression of a linked sequence can be tracked, thereby providing a useful so-called screenable or scorable markers. The expression of the linked protein can be detected without destroying tissue. More recently, interest has increased in utilization of screenable or scorable markers. By way of example without limitation, the promoter can be linked with detectable markers including a β-glucuronidase, or uidA gene (GUS), which encodes an enzyme for which various chromogenic substrates are known (Jefferson, et al., (1986) *Proc. Natl. Acad. Sci. USA* 83:8447-8451); chloramphenicol acetyl transferase; alkaline phosphatase; a R-locus gene, which encodes a product that regulates the production of anthocyanin pigments (red color) in plant tissues (Dellaporta, et al., (1988) in *Chromosome Structure and Function*, Kluwer Academic Publishers, Appels and Gustafson eds., pp. 263-282; Ludwig, et al., (1990) *Science* 247:449); a p-lactamase gene (Sutcliffe, (1978) *Proc. Nat'l. Acad. Sci. U.S.A.* 75:3737), which encodes an enzyme for which various chromogenic substrates are known (e.g., PADAC, a chromogenic cephalosporin); a xylE gene (Zukowsky, et al., (1983) *Proc. Nat'l. Acad. Sci. U.S.A.* 80:1101), which encodes a catechol dioxygenase that can convert chromogenic catechols; an α-amylase gene (Ikuta, et al., (1990) *Biotech.* 8:241); a tyrosinase gene (Katz, et al., (1983) *J. Gen. Microbiol.* 129:2703), which encodes an enzyme capable of oxidizing tyrosine to DOPA and dopaquinone, which in turn condenses to form the easily detectable compound melanin a green fluorescent protein (GFP) gene (Sheen, et al., (1995) *Plant J.* 8(5):777-84); a lux gene, which encodes a luciferase, the presence of which may be detected using, for example, X-ray film, scintillation counting, fluorescent spectrophotometry, low-light video cameras, photon counting cameras or multiwell luminometry (Teeri, et al., (1989) *EMBO J.* 8:343); DS-RED EXPRESS (Matz, et al., (1999) *Nature Biotech.* 17:969-973, Bevis, et al., (2002) *Nature Biotech* 20:83-87, Haas, et al., (1996) *Curr. Biol.* 6:315-324); *Zoanthus* sp. yellow fluorescent protein (ZsYellow) that has been engineered for brighter fluorescence (Matz, et al., (1999) *Nature Biotech.* 17:969-973, available from BD Biosciences Clontech, Palo Alto, Calif., USA, catalog no. K6100-1); and cyan florescent protein (CYP) (Bolte, et al., (2004) *J. Cell Science* 117:943-54 and Kato, et al., (2002) *Plant Physiol* 129:913-42).

A transformation vector comprising the particular regulatory sequences of the present invention, operably linked to an isolated polynucleotide sequence of interest in an expression cassette, can be used to transform any plant. In this manner, genetically modified plants, plant cells, plant tissue, and the like can be obtained. Transformation protocols can vary depending on the type of plant or plant cell, i.e., monocot or dicot, targeted for transformation. Suitable methods of transforming plant cells include microinjection, Crossway, et al., (1986) *Biotechniques* 4:320-334; electroporation, Riggs, et al., (1986) *Proc. Natl. Acad. Sci. USA* 83:5602-5606; *Agrobacterium*-mediated transformation, see, for example, Townsend, et al., U.S. Pat. No. 5,563,055; direct gene transfer, Paszkowski, et al., (1984) *EMBO J.* 3:2717-2722; and ballistic particle acceleration, see, for example, Sanford, et al., U.S. Pat. No. 4,945,050, Tomes, et al., (1995) in *Plant Cell, Tissue, and Organ Culture: Fundamental Methods*, ed. Gamborg and Phillips (Springer-Verlag, Berlin); and McCabe, et al., (1988) *Biotechnology* 6:923-926. Also see, Weissinger, et al., (1988) *Annual Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Datta, et al., (1990) *Bio/Technology* 8:736-740 (rice); Klein, et al., (1988) *Proc. Natl. Acad.*

*Sci. USA* 85:4305-4309 (maize); Klein, et al., (1988) *Biotechnology* 6:559-563 (maize); Klein, et al., (1988) *Plant Physiol.* 91:440-444 (maize); Fromm, et al., (1990) *Biotechnology* 8:833-839; Hooydaas-Van Slogteren, et al., (1984) *Nature* (London) 311:763-764; Bytebier, et al., (1987) *Proc. Natl. Acad. Sci. USA* 84:5345-5349 (Liliaceae); De Wet, et al., (1985) in *The Experimental Manipulation of Ovule Tissues*, ed. G. P. Chapman, et al., (Longman, New York), pp. 197-209 (pollen); Kaeppler, et al., (1990) *Plant Cell Reports* 9:415-418; and Kaeppler, et al., (1992) *Theor. Appl. Genet.* 84:560-566 (whisker-mediated transformation); D. Halluin, et al., (1992) *Plant Cell* 4:1495-1505 (electroporation); Li, et al., (1993) *Plant Cell Reports* 12:250-255 and Christou, et al., (1995) *Annals of Botany* 75:407-413 (rice); Osjoda, et al., (1996) *Nature Biotechnology* 14:745-750 (maize via *Agrobacterium tumefaciens*).

The cells that have been transformed can be grown into plants in accordance with conventional methods. See, for example, McCormick, et al., (1986) *Plant Cell Reports* 5:81-84. These plants can then be grown and pollinated with the same transformed strain or different strains. The resulting plant having stress-induced expression of the desired phenotypic characteristic can then be identified. Two or more generations can be grown to ensure that stress-induced expression of the desired phenotypic characteristic is stably maintained and inherited.

The following examples are offered by way of illustration and not by way of limitation.

EXAMPLES

As the coding regions for ZmCBF1 and ZmCBF2 had previously been isolated, 5' regulatory regions were isolated from maize plants via GenomeWalker™ (Clontech) and cloned. Isolated promoter regions were analyzed for cis elements and compared to *Arabidopsis* and rice CBF promoters.
Transformation of Maize by Particle Bombardment Immature maize embryos from greenhouse donor plants are bombarded with a plasmid containing an expression cassette comprising the ZmCBF1 or ZmCBF2 promoter operably linked to a gene of interest. The plasmid also comprises a selectable marker gene, for example PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

The ears are husked and surface sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 5 hours and then aligned within the 2.5 cm target zone in preparation for bombardment.

A plasmid vector is made which comprises the ZmCBF1 or ZmCBF2 promoter sequence operably linked to a gene of interest. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #5 in particle gun #HE35-1 or #HE35-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-5 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored under various conditions and compared to control plants. Marker gene expression is observed to confirm transformation. Alterations in phenotype, reflecting expression of the gene of interest, are monitored.

Bombardment medium (560Y) comprises 5.0 g/l N6 basal salts (SIGMA C-1516), 1.0 ml/l Eriksson's Vitamin Mix (1000×SIGMA-1511), 0.5 mg/l thiamine HCl, 120.0 g/l sucrose, 1.0 mg/l 2,5-D, and 2.88 g/l L-proline (brought to volume with D-1 $H_2O$ following adjustment to pH 5.8 with KOH); 2.0 g/l Gelrite® gelling agent (added after bringing to volume with D-I $H_2O$); and 8.5 mg/l silver nitrate (added after sterilizing the medium and cooling to room temperature). Selection medium (560R) comprises 5.0 g/l N6 basal salts (SIGMA C-1516), 1.0 ml/l Eriksson's Vitamin Mix (1000× SIGMA-1511), 0.5 mg/l thiamine HCl, 30.0 g/l sucrose, and 2.0 mg/l 2,5-D (brought to volume with D-I $H_2O$ following adjustment to pH 5.8 with KOH); 3.0 g/l Gelrite® gelling agent (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 5.3 g/l MS salts (GIBCO 11117-075), 5.0 ml/l MS vitamins stock solution (0.100 g nicotinic acid, 0.02 g/l thiamine HCL, 0.10 g/l pyridoxine HCL, and 0.50 g/l glycine brought to volume with polished D-I $H_2O$) (Murashige and Skoog (1962) *Physiol. Plant.* 15:573), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite® gelling agent (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 5.3 g/l MS salts (GIBCO 11117-075), 5.0 ml/l MS vitamins stock solution (0.100 g/l nicotinic acid, 0.02 g/l thiamine HCL, 0.10 g/l pyridoxine HCL, and 0.50 g/l glycine brought to volume with polished D-I $H_2O$), 0.1 g/l myo-inositol, and 50.0 g/l sucrose (brought to volume with polished D-I $H_2O$ after adjusting pH to 5.6); and 6 g/l Bacto™ Agar solidifying agent (added after bringing to volume with polished D-I $H_2O$), sterilized and cooled to 60° C.

Example 2

Transformation and Regeneration of Maize Callus via *Agrobacterium*

For *Agrobacterium*-mediated transformation of maize with the ZmCBF1 or ZmCBF2 promoter sequence (SEQ ID NO: 1 or 2) operably linked to a gene of interest, the method of Zhao is employed (U.S. Pat. No. 5,981,840, and PCT Patent Publication WO98/32326, the contents of which are hereby incorporated by reference). The immature embryos are cultured on solid medium with a selective agent resulting in the selective growth of transformed cells. The callus is then regenerated into plants, and calli grown on selective medium are cultured on solid medium to regenerate the plants.

The plants are monitored for a modulation in phenotype when compared to an appropriate control plant.

Details of *Agrobacterium* transformation may be as set out below or as known to one of skill in the art.

Preparation of *Agrobacterium* Suspension

*Agrobacterium* is streaked out from a −80° C. frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH$_2$O (stock solution A: K$_2$HPO$_4$ 60.0 g/l, NaH$_2$PO$_4$ 20.0 g/l, adjust pH to 7.0 w/KOH and autoclaved; stock solution B: NH$_4$Cl 20.0 g/l, MgSO$_4$.7H$_2$O 6.0 g/l, KCl 3.0 g/l, CaCl$_2$ 0.20 g/l, FeSO$_4$.7H$_2$O 50.0 mg/l, autoclaved; stock solution C: glucose 5.56 g/l, agar 16.67 g/l (#A-7049, Sigma Chemicals, St. Louis, Mo.) and autoclaved).

The plate can be stored at 4° C. and used usually for about 1 month. A single colony is picked from the master plate and streaked onto a plate containing PHI-M medium [yeast extract (Difco) 5.0 g/l; peptone (Difco)10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2,4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) are added to a 14 ml Falcon tube in a hood. About 3 full loops (5 mm loop size) *Agrobacterium* are collected from the plate and suspended in the tube, then the tube is vortexed to make an even suspension. One ml of the suspension is transferred to a spectrophotometer tube and the OD of the suspension is adjusted to 0.72 at 550 nm by adding either more *Agrobacterium* or more of the same suspension medium, for an *Agrobacterium* concentration of approximately 0.5×109 cfu/ml to 1×109 cfu/ml. The final *Agrobacterium* suspension is aliquoted into 2 ml microcentrifuge tubes, each containing 1 ml of the suspension. The suspensions are then used as soon as possible.

Embryo Isolation, Infection and Co-cultivation

About 2 ml of the same medium (here PHI-A or PHI-I) which is used for the *Agrobacterium* suspension is added into a 2 ml microcentrifuge tube. Immature embryos are isolated from a sterilized ear with a sterile spatula (Baxter Scientific Products S1565) and dropped directly into the medium in the tube. A total of about 100 embryos are placed in the tube. The optimal size of the embryos is about 1.0-1.2 mm. The cap is then closed on the tube and the tube is vortexed with a Vortex Mixer (Baxter Scientific Products S8223-1) for 5 sec. at maximum speed. The medium is removed and 2 ml of fresh medium are added and the vortexing repeated. All of the medium is drawn off and 1 ml of *Agrobacterium* suspension is added to the embryos and the tube is vortexed for 30 sec. The tube is allowed to stand for 5 min. in the hood. The suspension of *Agrobacterium* and embryos is poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; silver nitrate 0.85 mg/l; Gelrite® gelling agent (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2,4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube are transferred to the plate using a sterile spatula. The *Agrobacterium* suspension is drawn off and the embryos placed axis side down on the media. The plate is sealed with Parafilm® tape or Pylori Vegetative Combine Tape (product named "E.G.CUT" and available in 18 mm×50 m sections; Kyowa Ltd., Japan) and is incubated in the dark at 23-25° C. for about 3 days of co-cultivation.

Resting, Selection and Regeneration Steps

For the resting step, all of the embryos are transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2,4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate is sealed with Parafilm® or Pylon tape and incubated in the dark at 28° C. for 3-5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation For selection, all of the embryos are then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K. K., Tokyo, Japan) 1.5 mg/l for the first two weeks followed by 3 mg/l for the remainder of the time.; pH 5.8] putting about 20 embryos onto each plate.

The plates are sealed as described above and incubated in the dark at 28° C. for the first two weeks of selection. The embryos are transferred to fresh selection medium at two-week intervals. The tissue is subcultured by transferring to fresh selection medium for a total of about 2 months. The herbicide-resistant calli are then "bulked up" by growing on the same medium for another two weeks until the diameter of the calli is about 1.5-2 cm.

For regeneration, the calli are then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1-3 weeks to allow somatic embryos to mature. The calli are then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; Gelrite® gelling agent 1.5 g/l; pH 5.6] at 25° C. under a daylight schedule of 16 hrs. light (270 uE m-2sec-1) and 8 hrs. dark until shoots and roots are developed. Each small plantlet is then transferred to a 25×150 mm tube containing PHI-F medium and is grown under the same conditions for approximately another week. The plants are transplanted to pots with soil mixture in a greenhouse. Transformation events are determined at the callus stage or regenerated plant stage.

Ability of the ZmCBF1 or ZmCBF2 promoter to drive expression in maize is confirmed by marker gene detection in plant tissue.

Although the foregoing invention has been described in some detail by way of illustration and example for purposes of clarity of understanding, it will be obvious that certain changes and modifications may be practiced within the scope of the appended claims. All references cited are incorporated herein by reference.

That which is claimed:

1. An expression cassette comprising a polynucleotide of positions 1 through 1329 of SEQ ID NO: 1 operably linked to a polynucleotide of interest, wherein the polynucleotide of positions 1 through 1329 of SEQ ID NO:1 is heterologous to the polynucleotide of interest.

2. A vector comprising the expression cassette of claim 1.

3. A plant cell having stably incorporated into its genome the expression cassette claim 1.

4. The plant cell of claim 3, wherein said plant cell is from a monocot.

5. The plant cell of claim 4, wherein said monocot is maize, barley, wheat, oat, rye, sorghum or rice.

6. A plant having stably incorporated into its genome the expression cassette of claim 1.

7. The plant of claim 6, wherein said plant is a monocot.

8. The plant of claim 7, wherein said monocot is maize, barley, wheat, oat, rye, sorghum or rice.

9. A transgenic seed of the plant of claim 6.

10. The plant of claim 6, wherein the polynucleotide of interest encodes a gene product that confers drought tolerance, cold tolerance or salt tolerance.

11. The plant of claim 6, wherein the polynucleotide of interest encodes a polypeptide involved in nitrogen use efficiency, root lodging resistance, corn rootworm resistance, carbohydrate metabolism, protein metabolism, fatty acid metabolism or phytohormone biosynthesis.

12. A method for expressing a polynucleotide of interest in a plant, said method comprising introducing into the plant an expression cassette comprising a promoter and the polynucleotide of interest operably linked thereto, wherein said promoter comprises a polynucleotide of positions 1 through 1329 of SEQ ID NO: 1, and whereby the polynucleotide of interest is expressed in the plant.

13. The method of claim 12, wherein said plant is a monocot.

14. The method of claim 13, wherein said monocot is maize, barley, wheat, oat, rye, sorghum or rice.

15. The method of claim 12, wherein said polynucleotide of interest encodes a gene product that confers drought tolerance, cold tolerance or salt tolerance.

16. The method of claim 12, wherein said polynucleotide of interest encodes a polypeptide involved in nitrogen use efficiency, root lodging resistance, corn rootworm resistance, carbohydrate metabolism, protein metabolism, fatty acid metabolism or phytohormone biosynthesis.

17. A method for expressing a polynucleotide of interest in a plant cell, said method comprising introducing into the plant cell an expression cassette comprising a promoter and the polynucleotide of interest operably linked thereto, wherein said promoter comprises a polynucleotide of positions 1 through 1329 of SEQ ID NO: 1, and whereby the polynucleotide of interest is expressed in the plant cell.

18. The method of claim 17, wherein said polynucleotide of interest encodes a gene product that confers drought tolerance, cold tolerance or salt tolerance.

19. The method of claim 17, wherein said polynucleotide of interest encodes a polypeptide involved in nitrogen use efficiency, root lodging resistance, corn root worm resistance, carbohydrate metabolism, protein metabolism, fatty acid metabolism, or phytohormone biosynthesis.

\* \* \* \* \*